US006492109B1

(12) United States Patent
Lescallet et al.

(10) Patent No.: US 6,492,109 B1
(45) Date of Patent: Dec. 10, 2002

(54) SUSCEPTIBILITY MUTATION 6495DELGC OF BRCA2

(75) Inventors: Jennifer L. Lescallet, Great Falls, VA (US); Denise B. Thurber, Silver Spring, MD (US)

(73) Assignee: Gene Logic, Inc., Gaithersburg, MD (US)

( * ) Notice: Subject to any disclaimer, the term of this patent is extended or adjusted under 35 U.S.C. 154(b) by 0 days.

(21) Appl. No.: 09/158,183

(22) Filed: Sep. 21, 1998

Related U.S. Application Data

(60) Provisional application No. 60/059,595, filed on Sep. 23, 1997.

(51) Int. Cl.[7] ............................. L12O 1/68; C07H 21/04
(52) U.S. Cl. ..................... 435/6; 536/24.31; 536/24.33; 536/23.1
(58) Field of Search .............................. 435/91.1, 320.1, 435/6, 69.1; 536/23.5, 24.31, 23.1, 24.3, 24.32, 24.33

(56) References Cited

U.S. PATENT DOCUMENTS

| | | | |
|---|---|---|---|
| 4,458,066 A | 7/1984 | Caruthers et al. | |
| 4,683,202 A | 7/1987 | Mullis | |
| 5,445,934 A | 8/1995 | Fodor et al. | 435/6 |
| 5,510,270 A | 4/1996 | Fodor et al. | 436/518 |
| 5,545,531 A | 8/1996 | Rava et al. | 435/6 |
| 5,547,839 A | 8/1996 | Dower et al. | 435/6 |
| 5,561,058 A | 10/1996 | Gelfand et al. | 435/912 |
| 5,582,989 A | 12/1996 | Caskey et al. | |
| 5,589,330 A | 12/1996 | Shuber | |
| 5,593,840 A | 1/1997 | Bhatnagar et al. | 435/6 |
| 5,624,803 A | 4/1997 | Noonberg et al. | 435/6 |
| 5,633,134 A | 5/1997 | Shuber | |
| 5,650,316 A | 7/1997 | Aggarwal et al. | 435/375 |
| 5,654,155 A | 8/1997 | Murphy et al. | 435/6 |
| 5,693,473 A | 12/1997 | Shattuck-Eidens et al. | 435/6 |
| 5,709,999 A | 1/1998 | Shattuck-Eidens et al. | 435/6 |
| 5,710,001 A | 1/1998 | Skolnich et al. | 435/6 |
| 5,726,019 A | 3/1998 | Sidransky | 435/6 |
| 5,747,282 A | 5/1998 | Skolnick et al. | 435/69.1 |
| 5,753,441 A | 5/1998 | Skolnick et al. | 435/6 |
| 5,756,294 A | 5/1998 | White et al. | |
| 5,858,669 A | 1/1999 | Levine | 435/6 |
| 5,891,857 A | 4/1999 | Holt et al. | 514/44 |
| 5,912,127 A | 6/1999 | Narod et al. | 435/6 |
| 5,948,643 A | 9/1999 | Rubinfeld et al. | 435/69.1 |
| 5,965,377 A | 10/1999 | Adams et al. | 435/7.23 |
| 6,033,857 A | 3/2000 | Tavtigian et al. | 435/6 |
| 6,045,997 A | 4/2000 | Futreal et al. | 435/6 |
| 6,051,379 A | 4/2000 | Lescallett et al. | 435/6 |
| 6,083,698 A | 7/2000 | Olson et al. | 435/6 |
| 6,124,104 A | 9/2000 | Tavtigian et al. | 435/7.2 |
| 6,130,322 A | 10/2000 | Murphy et al. | 536/23.1 |

FOREIGN PATENT DOCUMENTS

| | | |
|---|---|---|
| EP | 0699754 A1 | 6/1996 |
| EP | 0705902 A1 | 10/1996 |
| EP | 0705903 A1 | 10/1996 |
| GB | 2307477 A | 5/1997 |
| WO | WO 93 04200 | 4/1993 |
| WO | WO 9519369 | 7/1995 |
| WO | WO 97/19110 | * 5/1997 |
| WO | WO 9722689 | 6/1997 |
| WO | WO 9730108 | 8/1997 |

OTHER PUBLICATIONS

Hacie et al. Detection of heterozygous mutatios in BRCA1 using high density oligonucleotide arrays and two colour fluorescence analysis. Nature Genetics. vol., 14, pp. 441–447, Dec. 1996.*
Bertwistle et al. (1998) Functions of the BRCA1 and BRCA2 genes, Curr. Opin. Genet. Dev. 8, 14–20.
Couch et al. (1996) BRCA2 germline in male breast cancer cases and breast cancer families, Nat. Genet. 13, 123–125.
Friend et al. (1995) Breast cancer information on the web, Nat. Genet. 11, 238–239.
Gayther et al. (1997) Variation of risks of breast and ovarian cancer associated with different germline mutations of the BRCA2 gene, Nat. Genet. 15, 103–105.
Holt et al. (1996) Growth retardation and tumour inhibition by BRCA1, Nat. Genet. 12, 298–302.
Jensen et al. (1996) BRCA1 is secreted and exhibits properties of a granin, Nat. Genet. 12, 303–308.
Katagiri et al. (1998) Multiple possible sites of BRCA2 interacting with DNA repair protein RAD51, Genes Chromosomes Cancer 21, 217–222.
Miki et al. (1994) A strong candidate for the breast and ovarian cancer susceptibility gene BRCA1, Science 266, 66–71.
Phelan et al. (1996) Mutation analysis of the BRCA2 gene in 49 site–specific breast cancer families, Nat. Genet. 13, 120–122.
Rowell et al. (1994) Invited editorial: inherited predisposition to breast and ovarian cancer, Am. J. Hum. Genet. 55, 861–865.
Schubert et al. (1997) BRCA2 in american families with four or more cases of breast or ovarian cancer: recurrent and novel mutations, variable expression, penetrance and the possiblity of families whose cancer is not attributable to BRCA1 or BRCA2, Am. J. Hum. Genet. 60, 1031–1040.

(List continued on next page.)

*Primary Examiner*—Kenneth R. Horlick
*Assistant Examiner*—Cynthia Wilder
(74) *Attorney, Agent, or Firm*—Morgan, Lewis & Bockius LLP

(57) ABSTRACT

A new mutation has been found in the BRCA2 gene. The mutation is a twobase pair deletion of nucleotide 6495 at nucleotides 6495 of the published cDNA sequence of BRCA2. A process for identifying a sequence variation in a BRCA2 polynucleotide sequence is disclosed. The identification process includes allele specific sequence-based techniques assays of known sequence variations. The methods can be used for efficient and accurate detection of a mutation in a test BRCA2 gene sample.

20 Claims, No Drawings

OTHER PUBLICATIONS

Sharan et al. (1997) Embryonic lethality and radiation hypersensitivity mediated by Rad51 in mice lacking BRCA2, Nature 386, 804–810.

Teng et al. (1996) Low incidence of BRCA2 mutations in breast carcinoma and other cancers, Nat. Genet. 13, 241–244.

Thompson et al. (1995) Decreased expression of BRCA1 accelerates growth and is often present during sporadic breast cancer progression, Nat. Genet. 9, 444–449.

Wooster et al. (1995) Identification of the breast cancer susceptibility gene BRCA2, Nature 378, 789–792.

Wooster et al. (1994) Localization of a breast cancer susceptibiity gene, BRCA2, to chromosome 13q12–13, Science 265, 2088–2090.

Zhang et al. (1998) BRCA1, BRCA2, and DNA damage response: collision or collusion? Cell 92, 433–436.

Abbaszadegan, M.R.. et al., "Automated detection of prevalent mutations in BRCA1 and BRCA2 genes, using a flourogenic PCR allelic discrimination assay" *Genetic Testing* 1(3):171–180 (1998).

Beaucage, S.L. et al., "Deoxynucleoside Phosphoramidites—A New Class of Key Intermediates for Deoxypolynucleotide Synthesis" *Tetrahedron Letters* 22(20):1859–1862 (1981).

Berman, D.A., et al., "A common mutation in BRCA2 that predisposes to a variety of cancers is found in both Jewish ashkenazi and non–Jewish individuals" *Cancer Research* 56:3409–3414 (1996).

Bignell, G., et al., "The BRC repeats are conserved in mammalian BRCA2 proteins" *Human Molecular Genetics* 6(1):53–58 (1997).

Cheng, J.et al., "Microchip–based Devices for Molecular Diagnosis of Genetic Diseases" *Molecular Diagnosis* 1(3):183–200 (1996).

Conner, B.J., et al., "Detection of sickle cell $\beta^S$–globin allele by hybridization with synthetic oligonucleotides" *Proc. Natl. Acad. Sci. USA 80*:278–282 (1983).

Hacia, J. et al., "Detection of heterozygous mutation in BRCA1 using high density oligonucleotide arrays and two-–colour fluorescence analysis" *Nature Genetics 14*:441–447 (1996).

Ikuta, S., et al., "Dissociation kinetics of 19 base paired oligonucleotide–DNA duplexes containing different single mismatched base pairs" *Nucleic Acids Research 15*:797–811 (1987).

Landegren, U., et al., "A Ligase–Mediated Gene Detection Technique" *Science 241*:1007–1021 (1988).

Landegren, U., et al., "DNA Diagnostic–Molecular Techniques and Automation" *Science 242*:229–237 (1988).

Maniatis, T. et al., "Isolation of High–Molecular–Weight, Eukaryotic DNA from Cells Grown in Tissue Culture" *Molecular Cloning: A Laboratory Manual* Cold Spring Harbor, NY pp. 280–281 (1982).

Michalowsky, et al., "Combinatorial Probes for Identifications of 100 Known Mutations in Hundreds of Patient Samples Simultaneously Using MASDA (Multiplex Allele–Specific Diagnostic Assay)" *American Journal of Human Genetics 59*(4)A272 poster 1573 (1996).

Neuhausen, S., et al., "Recurrent BRCA2 6174delT mutation in Ashkenazi Jewish women affected by breast cancer" *Nature Genetics 13*:126–128 (1996).

Saiki,R., et al., "A Novel Method for the Detection of Polymorphic Restriction Sites by Cleavage of Oligonucleotide Probes: Application to Sickle–Cell Anemia" *Bio/Technology 3*:1008–1012 (1985).

Sanger, F., et al., "Cloning in SIngle–stranded Bacteriophage as an Aid to Rapid DNA Sequencing" *J. Mol. Biol. 143*:161–178 (1980).

Southern, E.M. "DNA chips: analyzing sequence by hybridization to oligonucleotides on a large scale" *Trends in Genetics 12*(3): 110–115 (1996).

Tavtigian, S.V., et al., "The complete BRCA2 gene and mutations in chromosome 13q–linked kindreds" *Nature Genetics 3*(12):333–(1996).

* cited by examiner

SEQUENCE LISTING

<160> NUMBER OF SEQ ID NOS: 4

<210> SEQ ID NO 1
<211> LENGTH: 17
<212> TYPE: DNA
<213> ORGANISM: Homo sapiens
<220> FEATURE:
<221> NAME/KEY: protein_bind
<222> LOCATION: (1)...(17)
<223> OTHER INFORMATION: BRCA2-11F

<400> SEQUENCE: 1
tacagcaagt ggaaagc                          17

<210> SEQ ID NO 2
<211> LENGTH: 19
<212> TYPE: DNA
<213> ORGANISM: Homo sapiens
<220> FEATURE:
<221> NAME/KEY: primer_bind
<222> LOCATION: (1)...(19)
<223> OTHER INFORMATION: BRCA2-11-R

<400> SEQUENCE: 2
aagtttcagt tttaccaat                        19

<210> SEQ ID NO 3
<211> LENGTH: 17
<212> TYPE: DNA
<213> ORGANISM: Homo sapiens
<220> FEATURE:
<221> NAME/KEY: primer_bind
<222> LOCATION: (1)...(17)

<400> SEQUENCE: 3
gaactgagca tagtctt                          17

<210> SEQ ID NO 4
<211> LENGTH: 17
<212> TYPE: DNA
<213> ORGANISM: Homo sapiens
<220> FEATURE:
<221> NAME/KEY: misc_binding
<222> LOCATION: (1)...(17)

<400> SEQUENCE: 4
gaactgaata gtcttca                          17

SUSCEPTIBILITY MUTATION 6495DELGC OF BRCA2

This Application claims priority to U.S. Provisional Application Ser. No. 60/059,595, filed Sep. 23, 1997, which is incorporated herein by reference.

FIELD OF THE INVENTION

This invention relates to a gene which predisposes individuals to breast and ovarian cancer. More specifically, this invention relates to a specific mutation in the BRCA2 gene. In addition, it also relates to a method for detecting the presence of the mutation.

BACKGROUND OF THE INVENTION

BRCA2, located on chromosome 13q 12-q13, consists of over 70 kb of genomic DNA. The coding sequence produces a protein of 3,418 amino acids. Although most of the exons are small, exons 10 and 11 represent approximately 60% of the entire coding region. Germline mutations of BRCA2 are predicted to account for approximately 35% of families with multiple case, early onset female breast cancer, and they are also associated with an increased risk of male breast cancer, ovarian cancer, prostate cancer and pancreatic cancer.

The location of one or more mutations in the BRCA2 gene provides a promising approach to reducing the high incidence and mortality associated with breast and ovarian cancer through the early detection of women at high risk. These women, once identified, can be targeted for more aggressive prevention programs. Screening is carried out by a variety of methods which include karyotyping, probe binding and DNA sequencing. In such cases where one or only a few known mutations are responsible for the disease, methods for detecting the mutations are targeted to the site within the gene at which they are known to occur.

There is a need in the art to identify mutations in the BRCA2 gene. Identification of mutations of the BRCA2 gene and protein would allow more widespread diagnostic screening for hereditary breast and ovarian cancer than is currently possible.

SUMMARY OF THE INVENTION

The present invention is based on the discovery of a two base pair deletion of nucleotide 6495 of the published BRCA2 cDNA sequence which is associated with susceptibility to and development of breast and ovarian cancer.

It is an object of the invention to provide a method for determining a predisposition or higher susceptibility to breast and ovarian cancer.

It is another object of the invention to provide primers for detecting and amplifying a region of DNA which contains the 6495delGC mutation.

DETAILED DESCRIPTION OF THE PREFERRED EMBODIMENTS

The present invention is based on the discovery of a two base pair deletion of nucleotide 6495 of the published BRCA2 cDNA sequence. This deletion mutation is referred to as 6495delGC. The BRCA2 gene is a tumor suppressor gene associated with breast and ovarian cancer.

The 6495delGC interrupts the normal reading frame of the BRCA2 transcript, resulting in the appearance of an in-frame terminator TAG at codon position 2090. This mutation is, therefore, predicted to result in a truncated, and most likely, non-functional protein.

Useful DNA molecules according to the invention are those which will specifically hybridize to BRCA2 sequences in the region of the 6495delGC mutation. Typically these are 17 to 20 nucleotides in length and have the nucleotide sequence corresponding to the region of the 6495delGC mutation at nucleotides 6495 of the BRCA2 cDNA sequence. Such molecules can be labeled, according to any technique known in the art, such as with radiolabels, fluorescent labels, enzymatic labels, sequence tags, etc. According to another aspect of the invention, the DNA molecules contain the 6495delGC mutation. Such molecules can be used as allele-specific oligonucleotide probes to track a particular mutation through a family.

Blood samples can be tested to determine whether the BRCA2 gene contains the 6495delGC mutation. In one embodiment of the invention a pair of isolated oligonucleotide primers are provided.

BRCA2-11F: 5'-TAC AGC AAG TGG AAA GC-3'(SEQ ID NO: 1), and BRCA2-11-R: 5'-AAG TTT CAG TTT TAC CAA T-3'(SEQ ID NO:2). The designation BRCA2-11 refers to a sequence in exon 11 of the BRCA2 gene. F and R refer to forward and reverse. The oligonucleotide primers are useful in direct amplification of a target polynucleotide prior to sequencing. These unique BRCA2 exon 11 oligonucleotide primers were designed and produced at Oncormed based upon identification of the 6495delGC mutation.

In another embodiment of the invention a pair of isolated allele specific oligonucleotides are provided.

5'-GAA CTG AGC ATA GTC TT-3'(SEQ ID NO:3), and

5'-GAA CTG AAT AGT CTT CA-3'(SEQ ID NO:4).

The allele specific oligonucleotides are useful in diagnosis of a subject at risk of having breast or ovarian cancer. The allele specific oligonucleotides hybridize with a target polynucleotide sequence containing the 6495delGC mutation. 5'-GAA CTG AGC ATA GTC TT-3'(SEQ ID NO:3) hybridizes preferentially to the wildtype sequence and is useful as a control sequence. 5'-GAA CTG AAT AGT CTT CA-3' (SEQ ID NO:4) is designed to hybridize preferentially to the mutant sequence.

The term "substantially complementary to" or "substantially the sequence" refers to (e.g., SEQ ID NO:3 and SEQ ID NO:4) sequences which hybridize to the sequences provided under stringent conditions and/or sequences having sufficient homology with SEQ ID NO:3 and SEQ ID NO:4, such that the allele specific oligonucleotides of the invention hybridize to the sequence. The term "isolated" as used herein includes oligonucleotides substantially free of other nucleic acids, proteins, lipids, carbohydrates or other materials with which they may be associated. Such association being either in cellular material or in a synthesis medium. A "target polynucleotide" refers to the nucleic acid sequence of interest e.g., the BRCA2 encoding polynucleotide. Other primers which can be used for primer hybridization will be known or readily ascertainable to those of skill in the art.

The primers of the invention embrace oligonucleotides of sufficient length and appropriate sequence so as to provide initiation of polymerization on a significant number of nucleic acids in the polymorphic locus. Specifically, the term "primer" as used herein refers to a sequence comprising two or more deoxyribonucleotides or ribonucleotides, preferably more than three, and more preferably more than eight and most preferably at least 20 nucleotides of the BRCA2 gene wherein said DNA sequence contains the 6495delGC mutation relative to BRCA2 contained in SEQ ID NO's:3 and 4. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of the primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et. al., *Tetrahedron Letters*, 22:1859–1862 (1981). One method for synthesizing oligonucleotides on a modified solid support is described in U.S. Pat. No. 4,458,066.

Any nucleic acid specimen, in purified or nonpurified form, can be utilized as the starting nucleic acid or acids, providing it contains, or is suspected of containing, the specific nucleic acid sequence containing the polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al., *Molecular Cloning: A Laboratory Manual*, Cold Spring Harbor, N.Y., pp. 280–281 (1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. PCR. A Practical Approach, ILR Press, Eds. M. J. McPherson, P. Quirke, and G. R. Taylor (1992).

The amplification products may be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., *Bio/Technology*, 3:1008–1012, 1985), allele-specific oligonucleotide (ASO) probe analysis (Conner, et. al., *Proc. Nat. Acad. Sci. U.S.A.*, 80:278, 1983), oligonucleotide ligation assays (OLAS) (Landgren, et. al., *Science*, 241:1007, 1988), and the like. Molecular techniques for DNA analysis have been reviewed (Landgren, et. al., *Science*, 242:229–237, 1988).

Preferably, the method of amplifying is by PCR, as described herein and as is commonly used by those of ordinary skill in the art. Alternative methods of amplification have been described and can also be employed as long as the BRCA2 locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter olignucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tagalong sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for hincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling. Another amplification system useful in the method of the invention is the QB Replicase System. Although PCR is the preferred method of amplification of the invention, these other methods can also be used to amplify the BRCA2 locus as described in the method of the invention.

In another embodiment of the invention a method is provided for diagnosing a subject having a predisposition or higher susceptibility to (at risk of) breast or ovarian cancer comprising sequencing a target nucleic acid of a sample from a subject by dideoxy sequencing following amplification of the target nucleic acid.

In another embodiment of the invention a method is provided for diagnosing a subject having a predisposition or higher susceptibility to (at risk of) breast or ovarian cancer, comprising contacting a target nucleic acid of a sample from a subject with a reagent that detects the presence of the 6495delGC mutation and detecting the mutation.

In another embodiment of the invention a method is provided for characterizing a tumor. One method comprises sequencing the target nucleic acid isolated from the tumor to determine if the 6495delGC has occured. Sanger, F., et. al., *J Mol. Biol.* 142:1617 (1980).

Another method comprises contacting a target nucleic acid of a sample from a subject with a reagent that detects the presence of the 6495delGC mutation and detecting the mutation. A number of hybridization methods are well known to those skilled in the art. Many of them are useful in carrying out the invention.

The materials for use in the method of the invention are ideally suited for the preparation of a diagnostic kit. Such a kit may comprise a carrier means being compartmentalized to receive in close confinement one or more container means such as vials, tubes, and the like, each of the container means comprising one of the separate elements to be used in the method. For example, one of the container means may comprise means for amplifying BRCA2 DNA, said means comprising the necessary enzyme(s) and oligonucleotide primers for amplifying said target DNA from the subject. The oligonucleotide primers include primers having a sequence:

BRCA-2-11F: 5'-TAC AGC AAG TGG AAA GC-3'(SEQ ID NO:1) or

5'-AAG TTT CAG TTT TAC CAA T-3'(SEQ ID NO:2)

or primer sequences substantially complementary or substantially homologous thereto. The target flanking 5' and 3' polynucleotide sequence has substantially the sequence selected from the group consisting of:

5'-GAA CTG AGC ATA GTC TT-3'(SEQ ID NO: 3), and

5'-GAA CTG AAT AGT CTT CA-3'(SEQ ID NO:4)

and sequences substantially complementary or homologous thereto. Other oligonucleotide primers for amplifying BRCA2 will be known or readily ascertainable to those of skill in the art.

The following definitions are provided for the purpose of understanding this invention.

"Coding sequence" or "DNA coding sequence" refers to those portions of a gene which, taken together, code for a peptide (protein), or which nucleic acid itself has function.

"Primer" as used herein refers to a sequence comprising about 20 or more nucleotides of a gene used to initiate DNA synthesis via the PCR.

A "target polynucleotide" refers to the nucleic acid sequence of interest e.g., the BRCA2 encoding polynucleotide.

"Consensus" means the most commonly occurring in the population.

"Substantially complementary to" refers to probe or primer sequences which hybridize to the sequences provided under stringent conditions and/or sequences having sufficient homology with test polynucleotide sequences, such that the allele specific oligonucleotide probe or primers hybridize to the test polynucleotide sequences to which they are complimentary.

"Isolated" as used herein refers to substantially free of other nucleic acids, proteins, lipids, carbohydrates or other materials with which they may be associated. Such association is typically either in cellular material or in a synthesis medium.

"Sequence variation" as used herein refers to any difference in nucleotide sequence between two different oligonucleotide or polynucleotide sequences.

"Polymorphism" as used herein refers to a sequence variation in a gene which is not associated with pathology.

"Mutation" as used herein refers to an altered genetic sequence which results in the gene coding for a non-functioning protein or a protein with substantially reduced or altered function. Generally, a deleterious mutation is associated with pathology or the potential for pathology. The mutations identified herein result in a premature stop codon.

"Pre-determined sequence variation" as used herein refers to a nucleotide sequence that is designed to be different than the corresponding sequence in a reference nucleotide sequence. A predetermined sequence variation can be a known mutation in a gene.

"Allele specific detection assay" as used herein refers to an assay to detect the presence or absence of a pre-determined sequence variation in a test polynucleotide or oligonucleotide by annealing the test polynucleotide or oligonucleotide with a polynucleotide or oligonucleotide of pre-determined sequence such that differential DNA sequence based techniques or DNA amplification methods discriminate between normal and mutant.

"Sequence variation locating assay" as used herein refers to an assay that detects a sequence variation in a test polynucleotide or oligonucleotide and localizes the position of the sequence variation to a sub-region of the test polynucleotide, without necessarily determining the precise base change or position of the sequence variation.

"Targeted confirmatory sequencing" as used herein refers to sequencing a polynucleotide in the region wherein a sequence variation has been located by a sequence variation locating assay in order to determine the precise base change and/or position of the sequence variation.

The invention in several of its embodiments includes:
Detection of Pre-determined Sequence Variations Stage I analysis is used to determine the presence or absence of a pre-determined nucleotide sequence variation; preferably a known mutation or set of known mutations in the test gene. In accordance with the invention, such pre-determined sequence variations are detected by allele specific hybridization, a sequence-dependent-based technique which permits discrimination between normal and mutant alleles. An allele specific assay is dependent on the differential ability of mismatched nucleotide sequences (e.g., normal:mutant) to hybridize with each other, as compared with matching (e.g., normal:normal or mutant:mutant) sequences.

Detection of Pre-determined Sequence Variations Using Allele Specific Hybridization A variety of methods well-known in the art can be used for detection of pre-determined sequence variations by allele specific hybridization. Preferably, the test gene is probed with allele specific oligonucleotides (ASOs); and each ASO contains the sequence of a known mutation. ASO analysis detects specific sequence variations in a target polynucleotide fragment by testing the ability of a specific oligonucleotide probe to hybridize to the target polynucleotide fragment. Preferably, the oligonucleotide contains the mutant sequence (or its complement). The presence of a sequence variation in the target sequence is indicated by hybridization between the oligonucleotide probe and the target fragment under conditions in which an oligonucleotide probe containing a normal sequence does not hybridize to the target fragment. A lack of hybridization between the sequence variant (e.g., mutant) oligonucleotide probe and the target polynucleotide fragment indicates the absence of the specific sequence variation (e.g., mutation) in the target fragment. In a preferred embodiment the test samples are probed in a standard dot blot format. Each region within the test gene that contains the sequence corresponding to the ASO is individually applied to a solid surface, for example, as an individual dot on a membrane. Each individual region can be produced, for example, as a separate PCR amplification product using methods well-known in the art (see, for example, the experimental embodiment set forth in Mullis, K. B., 1987, U.S. Pat. No. 4,683,202). The use of such a dot blot format is described in detail in one of the examples below, detailing the Stage I analysis of the human BRCA2 gene to detect the presence or absence of eight different known mutations using eight corresponding ASOS.

Membrane-based formats that can be used as alternatives to the dot blot format for performing ASO analysis include, but are not limited to, reverse dot blot, (multiplex amplification assay), and multiplex allele-specific diagnostic assay (MASDA).

In a reverse dot blot format, oligonucleotide or polynucleotide probes having known sequences are immobilized on the solid surface, and are subsequently hybridized with the labeled test polynucleotide sample.

In a multiplex format, individual samples contain multiple target sequences within the test gene, instead of just a single target sequence. For example, multiple PCR products each containing at least one of the ASO target sequences are applied within the same sample dot. Multiple PCR products can be produced simultaneously in a single amplification reaction using the methods of Caskey et. al., U.S. Pat. No. 5,582,989. The same blot, therefore, can be probed by each ASO whose corresponding sequence is represented in the sample dots.

A MASDA format expands the level of complexity of the multiplex format by using multiple ASOs to probe each blot (containing dots with multiple target sequences). This procedure is described in detail in U.S. Pat. No. 5,589,330 by A. P. Shuber, and in Michalowsky et. al., *American Journal of Human Genetics* 59(4):A272, poster 1573 (October 1996), each of which is incorporated herein by reference in its entirety. First, hybridization between the multiple ASO probe and immobilized sample is detected. This method relies on the prediction that the presence of a mutation among the multiple target sequences in a given dot is sufficiently rare that any positive hybridization signal results from a single ASO within the probe mixture hybridizing with the corresponding mutant target. The hybridizing ASO is then identified by isolating it from the site of hybridization and determining its nucleotide sequence.

Suitable materials that can be used in the dot blot, reverse dot blot, multiplex, and MASDA formats are well-known in the art and include, but are not limited to nylon and nitrocellulose membranes.

When the target sequences are produced by PCR amplification, the starting material can be chromosomal DNA in which case the DNA is directly amplified. Alternatively, the starting material can be mRNA, in which case. the mRNA is first reversed transcribed into cDNA and then amplified according to the well known technique of RT-PCR (see, for example, U.S. Pat. No. 5,561,058 by Gelfand et. al.).

The methods described above are suitable for moderate screening of a limited number of sequence variations. However, with the need in molecular diagnosis for rapid, cost effective large scale screening, technologies have developed that integrate the basic concept of ASO, but far exceed the capacity for mutation detection and sample number. These alternative methods to the ones described above include, but are not limited to, large scale chip array sequence-based techniques. The use of large scale arrays allows for the rapid analysis of many sequence variants. A review of the differences in the application and development of chip arrays is covered by Southern, E. M., *Trends In Genetics*, 12:110–115 (March 1996) and Cheng et. al., *Molecular Diagnosis*, 1:183–200 (September 1996). Several approaches exist involving the manufacture of chip arrays. Differences include, but not restricted to: type of solid support to attach the immobilized oligonucleotides, labeling techniques for identification of variants and changes in the sequence-based techniques of the target polynucleotide to the probe.

A promising methodology for large-scale analysis on 'DNA chips' is described in detail in Hacia et. al., *Nature Genetics* 14:441–447 (1996), which is hereby incorporated by reference in its entirety. As described in Hacia et. al., high density arrays of over 96,000 oligonucleotides, each 20 nucleotides in length, are immobilized to a single glass or silicon chip using light directed chemical synthesis. Contingent on the number and design of the oligonucleotide probe, potentially every base in a sequence can be interrogated for alterations. Oligonucleotides applied to the chip, therefore, can contain sequence variations that are not yet known to occur in the population, or they can be limited to mutations that are known to occur in the population.

Prior to hybridization with oligo probes on the chip, the test sample is isolated, amplified and labeled (e.g. fluorescent markers) by means well known to those skilled in the art. The test polynucleotide sample is then hybridized to the immobilized oligonucleotides. The intensity of sequence-based techniques of the target polynucleotide to the immobilized probe is quantitated and compared to a reference sequence. The resulting genetic information can be used in molecular diagnosis.

A common, but not limiting, utility of the 'DNA chip' in molecular diagnosis is screening for known mutations. However, this may impose a limitation to the technique by only looking at mutations that have been described in the field. The present invention allows allele specific hybridization analysis be performed with a far greater number of mutations than previously available. Thus, the efficiency and comprehensiveness of large scale ASO analysis will be broadened, reducing the need for cumbersome end-to-end sequence analysis, not only with known mutations but in a comprehensive manner all mutations which might occur as predicted by the principles accepted, and the cost and time associated with these cumbersome tests will be decreased.

EXAMPLES

Materials and Methods

Genomic DNA is isolated from white blood cells of a subject with a family history of breast cancer. Dideoxy sequence analysis is performed following polymerase chain reaction amplification of segment of exon 11.

Exon 11 of the BRCA2 gene is subjected to direct dideoxy sequence analysis by asymmetric amplification using the polyrnerase chain reaction (PCR) to generate a single stranded product amplified from this DNA sample. Shuldiner, et. al., Handbook of Techniques in Endocrine Research, pp. 457–486, DePablo, F., Scanes, C., eds., Academic Press, Inc. (1993). Fluorescent dye is attached for automated sequencing using the Taq Dye Terminator Kit (Perkin-Elner Cat. No. 401628). DNA sequencing is performed in both forward and reverse directions on an Applied Biosystems, Inc. (ABI) automated sequencer (Model 377). The software used for analysis of the resulting data is "Sequence Navigator" purchased through ABI.

Example 1

Detection of Sequence Variations In Polynucleotides

The methods of the invention, which can be used to detect sequence variations in any polynucleotide sample, are demonstrated in the example set forth in this section, for the purpose of illustration, for one gene in particular, namely, the human BRCA2 gene. The BRCA2 coding sequence is approximately 10,248 base pairs encoding the 3418 amino acid BRCA2 protein.

Allele-specific Oligonucleotide (ASO) Analysis of Mutations in the BRCA2 Gene

Designing an Allele Specific Oligonucleotide (ASO) Probe

An allele specific oligonucleotide probe is short, single stranded polynucleotide that is engineered to hybridize exactly to a target sequence under a given set of conditions. Routinely, ASO probes are designed to contain sequences identical to the normal allele and sequence variation respectively. Hybridization of the probe to the target allows for the discrimination of a variant sample. Under stringent conditions, a probe with a variation as simple as a single-base pair will not hybridize to a normal sequence due to a destabilizing effect of the normal-mutant duplex (Ikuta, S. et. al., *Nucleic Acids Research* 15:797–811 (1987). For use in this invention, probes were used to discriminate between a wild-type or normal sequence from one that is mutated. Each probe pair contained a polynucleotide sequence that encompassed an area that would identify a selected mutation in the BRCA2 gene.

The design of an ASO hybridization probe must meet two basic requirements. (Current Protocols in Human Genetics, 9.4, 1995). First, probes that are used together in the same pool should be around the same length. Although the standard length of a probe is optimally 17 base pairs, the range can be as short as 14 or as long as 24. Second, the mismatched region should not be placed at the end of the 17 base pair probe, but approximately in the middle of the sequence, 5–7 bases from the 5' end of the probe. In addition, the placement of a mismatch, in the case of a longer probe, should not be at the end, but at a position that allows strong hybridization and stabilization of the polynucleotide strand. In order to minimize the effects of variations in base composition of the probes, tetramethylammonium chloride is used as in the ASO hybrid's buffer (Shuber, T., U.S. Pat. No. 5,633,134). Conventionally, ASO probes are synthesized on a DNA synthesizer. They can be labeled with isotopic or non-isotopic detection agents using means familiar to those of skill in the art. The process outlined in this application for making and using probes can be applicable for other gene sequences.

Isolation of Genomic DNA

White blood cells were collected from the patient and genomic DNA is extracted from the white blood cells according to well-known methods (Sambrook, et. al., Molecular Cloning: A Laboratory Manual, 2nd Ed., 1989, Cold Spring Harbor Laboratory Press, at 9.16–9.19).

PCR Amplification

The genomic DNA is used as a template to amplify a separate DNA fragment encompassing the site of the mutation to be tested. The 25 µl PCR reaction contained the following components: 2 µl template (100 ng/µl) DNA, 2.5 µl 10×PCR Buffer (Perkin-Elmer), 1.5 µl dNTP (2 mM each dATP, dCTP, dGTP, dTTP), 1.5 µl Forward Primer (10 µM), 1.5 µl Reverse Primer (10 µM), 0.5 µl AmpliTaq Gold® Taq DNA Polymerase (Perkin-Elmer), 1.0 µl (25 mM) $MgCl_2$ and $dH_2O$ up to 25 µl. All reagents for each exon except the genomic DNA can be combined in a master mix and aliquoted into the reaction tubes as a pooled mixture.

For each exon analyzed, the following control PCRs were set up:
(1) "Negative" DNA control (100 ng placental DNA (Sigrna Chemical Co., St. Louis, Mo.)
(2) Three "no template" controls PCR for all exons is performed using the following thermocycling conditions:

| Temperature | Time | Number of Cycles |
| --- | --- | --- |
| 95° C. | 5 minutes | 1 cycle |
| 95° C. | 30 seconds | |
| 55° C. | 30 seconds | 30 cycles |
| 72° C. | 1 minute | |
| 72° C. | 5 minutes | 1 cycle |
| 4° C. | infinity | 1 cycle |

Quality control agarose gel of PCR amplification

The quality of the PCR products were examined prior to further analysis by electrophoresing an aliquot of each PCR reaction sample on an agarose gel. 5 µl of each PCR reaction is run on an agarose gel along side a DNA mass ladder (Gibco BRL Low DNA Mass Ladder, Cat. No. 10068-013). The electrophoresed PCR products were analyzed according to the following criteria:

Each patient sample must show a single band of the corresponding size (422 base pairs). If a patient sample demonstrates smearing or multiple bands, the PCR reaction must be repeated until a clean, single band is detected. If no PCR product is visible or if only a weak band is visible, but the control reactions with placental DNA template produced a clear band, the patient sample should be re-amplified with 2× as much template DNA.

All three "no template" reactions must show no amplification products. Any PCR product present in these reactions is the result of contamination. If any one of the "no template" reactions shows contamination, all PCR products should be discarded and the entire PCR set of reactions should be repeated after the appropriate PCR decontamination procedures have been taken.

The optimum amount of PCR product on the gel should be between 50 and 100 ng, which can be determined by comparing the intensity of the patient sample PCR products with that of the DNA mass ladder. If the patient sample PCR products contain less than 50 to 100 ng, the PCR reaction should be repeated until sufficient quantity is obtained.

Binding PCR Products to Nylon Membrane

The PCR products are denatured no more than 30 minutes prior to binding the PCR products to the nylon membrane. To denature the PCR products, the remaining PCR reaction (20 µl) and the appropriate positive control mutant gene amplification product are diluted to 200 µl final volume with PCR Diluent Solution (500 mM NaOH 2.0 M NaCl, 25 mM EDTA) and mixed thoroughly. The mixture is heated to 950° C. for 5 minutes, and immediately placed on ice and held on ice until loaded onto dot blotter, as described below.

The PCR products are bound to 9 cm by 12 cm nylon Zeta Probe Blotting Membrane (BioRad, Hercules, Calif., catalog number 162-0153) using a Bio-Rad dot blotter apparatus. Forceps and gloves are used at all times throughout the ASO analysis to manipulate the membrane, with care taken never to touch the surface of the membrane with bare hands.

Pieces of 3 MM filter paper [Whatman®, Clifton, N.J.] and nylon membrane are pre-wet in 10×SSC from 20×SSC buffer stock. The vacuum apparatus is rinsed thoroughly with $dH_2O$ prior to applying the membrane. 100 µl of each denatured PCR product sample is added to the wells of the blotting apparatus. Each row of the blotting apparatus contains a set of reactions for a single exon to be tested, including a placental DNA (negative) control, a synthetic oligonucleotide with the 6495delGC mutation (positive) control, and three no template DNA controls.

After applying PCR products, the nylon filter is placed DNA side up on a piece of 3 MM filter paper saturated with denaturing solution (1.5 M NaCl, 0.5 M NaOH) for 5 minutes. The membrane is transferred to a piece of 3 MM filter paper saturated with neutralizing solution (1M Tris-HCl, pH 8, 1.5 M NaCl) for 5 minutes. The neutralized membrane is then transferred to a dry 3 MM filter DNA side up, and exposed to ultraviolet light (Stralinker, Stratagene, La Jolla, Calif.) for exactly 45 seconds the fix the DNA to the membrane. This LTV crosslinking should be performed within 30 min. of the denaturation/neutralization steps. The nylon membrane is then cut into strips such that each strip contains a single row of blots of one set of reactions for a single exon.

Hybridizing Labeled Oligonucleotides to the Nylon Membrane Prehybridization

The strip is prehybridized at 12° C. incubation using the Hybaid® (Savant Instruments, Inc., Holbrook, N.Y.) hybridization apparatus. 2×SSC (15 to 20 ml) is preheated to 52° C. in a water bath. For each nylon strip, a single piece of nylon mesh cut slightly larger than the nylon membrane strip (approximately 1 "×5") is pre-wet with 2×SSC. Each single nylon membrane is removed from the prehybridization solution and placed on top of the nylon mesh. The membrane/mesh "sandwich" is then transferred onto a piece of parafilm. The membrane/mesh sandwich is rolled lengthwise and place into an appropriate Hybaid® bottle, such that the rotary action of the Hybaid® apparatus caused the membrane to unroll. The bottle is capped and gently rolled to cause the membrane/mesh to unroll and to evenly distribute the 2×SSC, making sure that no air bubbles formed between the membrane and mesh or between the mesh and the side of the bottle. The 2×SSC is discarded and replaced with 5 ml TAC HYBRIDIZATION Solution, which contained 3 M TAC (Sigma T-3411), 100 mM $Na_3PO_4$(pH6.8), 1 mM EDTA, 5×Denhardt's (1% Ficoll, 1% polyvinylpyrrolidone, 1% BSA (fraction V)), 0.6% SDS, and 100 ug/ml Herring Sperm DNA. The filter strips were prehybridized at 52° C. with medium rotation (approx. 8.5 setting on the Hybaid® speed control) for at least one hour. Prehybridization can also be performed overnight.

Labeling Oligonucleotides

The DNA sequences of the oligonucleotide probes used to detect the BRCA2 mutation are as follows (for each mutation, a mutant and a normal oligonucleotide must be labeled): 6495delGC-Normal: 5'-GAA CTG AGC ATA GTC TT-3'(SEQ ID NO:3), and 6495delGC-Mutant: 5'-GAA CTG AAT AGT CTT CA-3'(SEQ ID NO:4).

Each labeling reaction contains 2–15×Kinase buffer (or 1 µl of 10×kinase buffer), 5 µl gamma-ATP $^{37}$P (not more than one week old), 1 µl T4 polynucleotide kinase, 3 µl oligonucleotide (20 µM stock), sterile H$_2$O to 10 µl final volume if necessary. The reactions are incubated at 37° C. for 30 minutes, then at 65° C. for 10 minutes to heat inactivate the kinase. The kinase reaction is diluted with an equal volume of sterile dH$_2$O (10 µl).

The oligonucleotides are purified on STE Micro Select-D, G-25 spin columns (catalog no. 5303-356769), according to the manufacturer's instructions. The 20 µl synthetic oligonucleotide with the 6495delGC mutation eluate is diluted into 80 µl dH$_2$O. The amount of radioactivity in the oligonucleotide sample is determined by measuring the radioactive counts per minute (cpm). The total radioactivity must be at least 2 million cpm. For any samples containing less than 2 million total, the labeling reaction is repeated.

Hybridization with Mutant Oligonucleotides

Approximately 2–5 million counts the labeled mutant oligonucleotide probe is diluted into 5 mls of TAC hybridization solution, containing 40 µl of 20 µM stock of unlabeled normal oligonucleotide. The probe mix is preheated to 52° C. in the hybridization oven. The prehybridization solution is removed from each bottle and replaced with the probe mix. The filter is hybridized for 1 hour at 52° C. with moderate agitation. Following hybridization, the probe mix is decanted into a storage tube and stored at −20° C. The filter is rinsed by adding approximately 20 ml of 2×SSC+ 1.1% SDS at room temperature and rolling the capped bottle gently for approximately 30 seconds and pouring off the rinse. The filter for mutant 6495delGC is washed. The filter is washed with 2×SSC+0.1% SDS at room temperature for 20 to 30 minutes, with shaking.

The membranes are washed twice in 2×SSPE and 0.05% SDS at 60° C. for fifteen minutes. The membrane is wrapped in one layer of plastic wrap, placed on the autoradiography film, and exposed for at least five hours. The film is developed in an automatic film processor.

Control Hybridization with Normal Oligonucleotides

The purpose of this step is to ensure that the PCR products are transferred efficiently to the nylon membrane.

Following hybridization with the mutant oligonucleotide, as described above, each nylon membrane is washed in 2×SSC, 0.1% SDS for 20 minutes at 65° C. to melt off the mutant oligonucleotide. The nylon strip is prehybridized together in 35 ml of TAC hybridization solution for at least 1 hour at 52° C. in a shaking water bath. 2–5 million counts of each of the normal labeled oligonucleotide probes plus 40 µl of 20 µM stock of unlabeled normal oligonucleotide are added directly to the container containing the nylon membranes and the prehybridization solution. The filter and probes are hybridized at 52° C. with shaking for at least 1 hour. Hybridization can be performed overnight. The hybridization solution is poured off, and the nylon membrane is rinsed in 2×SSC, 0.1% SDS for 1 minute with gentle swirling by hand. The rinse is poured off and the membrane is washed in 2×SSC, 0.1% SDS at room temperature for 20 minutes with shaking.

The nylon membrane is removed and blotted. The nylon membrane is wrapped in one layer of plastic wrap and placed on autoradiography film, except that exposure is for at least 1 hour.

For each sample, adequate transfer to the membrane is indicated by a strong autoradiographic hybridization signal. For each sample, an absent or weak signal when hybridized with its normal oligonucleotide, indicates an unsuccessful transfer of PCR product, and it is a false negative. The ASO analysis must be repeated for any sample that did not successfully transfer to the nylon membrane.

Interpreting Results

After hybridizing with mutant oligonucleotides, the results for each exon are interpreted as follows:

TABLE 4A

| Result | | | | | Interpretation | Action |
|---|---|---|---|---|---|---|
| ● (+) | ○ (−) | ○ NT | ○ NT | ○ NT | All controls indicate assay is successful | Record results - dark circles are mutation positive, and all others are negative |
| ● (+) | ● (−) | ○ NT | ○ NT | ○ NT | Assay non-specific - mutant oligonucleotide hybridizing to normal DNA | Rewash membrane 30 minutes longer at appropriate temp. and re-expose |
| ○ (+) | ○ (−) | ○ NT | ○ NT | ○ NT | Mutant oligonucleotide probe is either washed off or did not label well enough, or PCR product is not transferred to membrane efficiently | Rehybridize with remaining labeled oligonucleotide. If still no signal, perform normal oligonucleotide hybridization, as above, to test transfer of PCR to membrane |
| ● (+) | ○ (−) | ◉ NT | ◉ NT | ◉ NT | Positive and negative controls indicate assay is successful, but PCR is contaminated | Perform standard clean up procedures for PCR contamination |

After hybridization with normal oligonucleotides, interpret the results as follows:

TABLE 4B

| Result | | | | | Interpretation | Action |
|---|---|---|---|---|---|---|
| ● (+) | ● (−) | ○ NT | ○ NT | ○ NT | Results indicate transfer of PCR products to membrane is successful. | Record results. |
| ● (+) | ● (−) | ○ #1 | ○ NT | ○ NT | Results indicate transfer of patient sample #1 is inefficient. May get false negative from this sample. | This sample will have to be transferred to another membrane and the assay repeated. |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

We claim:

1. An isolated oligonucleotide that specifically hybridizes to a BRCA2 nucleotide sequence, wherein the BRCA2 nucleotide sequence comprises a two nucleotide deletion corresponding to positions 8 and 9 of SEQ ID NO: 3, relative to a BRCA2 nucleotide sequence that does not contain the deletion.

2. The isolated oligonucleotide of claim 1, wherein the BRCA2 nucleotide sequence encodes a protein of about 3418 amino acids.

3. The isolated oligonucleotide of claim 1, wherein the BRCA2 nucleotide sequence that encodes a BRCA2 protein is about 10,248 nucleotides.

4. The isolated oligonucleotide of claim 1, wherein the two base deletion is a deletion of GC.

5. The isolated oligonucleotide of claim 1, consisting essentially of the sequence 5'-GAA CTG AAT AGT CTT CA-3'(SEQ ID NO: 4).

6. An isolated oligonucleotide that specifically hybridizes to a BRCA2 nucleotide sequence, wherein the BRCA2 nucleotide sequence comprises a stop codon beginning at a position corresponding to position 9 of SEQ ID NO: 3, relative to a BRCA2 nucleotide sequence that does not contain the stop codon.

7. The isolated oligonucleotide of claim 6, wherein the stop codon is TAG, TAA or TGA.

8. The isolated oligonucleotide of claim 7, wherein the stop codon is TAG.

9. An isolated oligonucleotide that specifically hybridizes to a BRCA2 nucleotide sequence corresponding to positions 9 to 11 of SEQ ID NO: 3, relative to a BRCA2 nucleotide sequence comprising a two nucleotide deletion corresponding to positions 8 and 9 of SEQ ID NO: 3.

10. The isolated oligonucleotide of claim 9, wherein the two base deletion is a deletion of GC.

11. The isolated oligonucleotide of claim 9, consisting of the sequence 5'-GAA CTG AGC ATA GTC TT-3'(SEQ ID NO: 3).

12. An isolated oligonucleotide consisting of the sequence 5'-TAC AGC AAG TGG AAA GC (SEQ ID NO: 1).

13. An isolated oligonucleotide consisting of the sequence 5'-AAG TTT CAG TTT TAC CAA T-3'(SEQ ID NO: 2).

14. An isolated oligonucleotide of any one of claims 1, 6, or 9, wherein the oligonucleotide is at least about 14 nucleotides in length.

15. An isolated oligonucleotide of any one of claims 1, 6, or 9, wherein the oligonucleotide is at least about 17 nucleotides in length.

16. An isolated oligonucleotide of any one of claims 1, 6, or 9, wherein the oligonucleotide is at least about 20 nucleotides in length.

17. An isolated oligonucleotide of any one of claims 1, 6, or 9, wherein the oligonucleotide is at least about 23 nucleotides in length.

18. The isolated oligonucleotide of any one of claims 1, 6, or 9, which is labeled.

19. The isolated oligonucleotide of claim 18, wherein the label is selected from the group consisting of a radiolabel, a fluorescent label, a bioluminescent label, a chemiluminescent label and an enzyme label.

20. A chip array comprising an oligonucleotide selected from any one of claims 1, 6, or 9.

\* \* \* \* \*